US00PP10726P

United States Patent [19]

Barth

[11] Patent Number: Plant 10,726

[45] Date of Patent: Dec. 15, 1998

[54] ECHINODORUS PLANT NAMED 'INDIAN RED'

[76] Inventor: Hans Barth, Ruhrstr. 30, 06846 Dessau, Germany

[21] Appl. No.: 853,887

[22] Filed: May 9, 1997

[51] Int. Cl.[6] ..... A01H 5/00

[52] U.S. Cl. ..... Plt./87.16

[58] Field of Search ..... Plt./87.16

[56] References Cited

PUBLICATIONS

Anthony Huxley; The New Royal Horticultural Society Dictionary of Gardening; pp. 132–133; 1992.

Dick Mills; You and Your Aquarium; pp. 112–197 and 264–273; 1992.

*Primary Examiner*—Howard J. Locker
*Assistant Examiner*—Kent L. Bell
*Attorney, Agent, or Firm*—C. A. Whealy

[57] ABSTRACT

A distinct cultivar of Echinodorus plant named 'Indian Red', characterized by its relatively compact plant habit; moderate vigor and moderate growth rate; and attractive brownish red leaves that are elliptic to ovate and undulating with upturned leaf apices.

2 Drawing Sheets

The present invention relates to a new and distinct cultivar of Echinodorus plant, botanically known as *Echinodorus aschersonianus×horemanii red*, and hereinafter referred to by the cultivar name 'Indian Red'.

The new cultivar is a product of a planned breeding program conducted by the inventor in Dessau, Germany. The new cultivar originated from a cross by the inventor between an unnamed plant of *Echinodorus aschersonianus* as the female or seed parent and an unnamed plant of *Echinodorus horemanii red* as the male or pollen parent. The cultivar 'Indian Red' was discovered and selected by the inventor as a plant within the progeny of the stated cross in a controlled environment in Dessau, Germany, in June, 1996. This selection was selected based on its moderate vigor, compact growth habit and desirable leaf color and leaf shape.

The new Echinodorus differs from its female parent, the species *Echinodorus aschersonianus*, in the following characteristics:

1. Leaf color of plants of the new Echinodorus is brownish red whereas leaf color of plants of the species *Echinodorus aschersonianus* is green.

2. Leaf shape and leaf apices of plants of the species *Echinodorus aschersonianus* are more rounded than leaves of plants of the new Echinodorus.

3. Leaves of plants of the new Echinodorus are undulating and leaf apices are upturned whereas leaves of plants of the species *Echinodorus aschersonianus* are flat.

The new Echinodorus differs from its male parent, the species *Echinodorus horemanii red*, in the following characteristics:

1. Plants of the new Echinodorus are more compact than plants of the species *Echinodorus horemanii red.*

2. Leaves of plants of the new Echinodorus are shorter than leaves of the plants of the species *Echinodorus horemanii red.*

Asexual propagation of the new cultivar by tissue culture at Dessau, Germany, has shown that the unique features of this new Echinodorus plant are stable and reproduced true to type in successive generations of asexual propagation.

The new Echinodorus has not been observed under all possible enviromental conditions. The phenotype may vary somewhat with variations in environment such as temperature and light intensity, without, however, any variance in genotype. In addition, the appearance of plants grown in an aerial environment may differ from the appearance of plants grown in an aquatic environment. The following observations, measurements and comparisons describe plants grown in Berlin, Germany, in a glass greenhouse in an aquatic environment with average day and night temperatures of 25° C.

The new Echinodorus can only be grown in fresh water. A pH of 6.5 to 7.8 and me/L of less than 30 are recommended for optimum growth.

The following traits have been repeatedly observed and are determined to be the unique characteristics of 'Indian Red'. These characteristics in combination distinguish 'Indian Red' as a new and distinct cultivar:

1. Relatively compact plant habit.
2. Moderate vigor and moderate growth rate.
3. Attractive brownish red leaves that are elliptic to ovate and undulating with upturned leaf apices.

The new Echinodorus is similar to the species *Echinodorus barthii*. The species *Echinodorus barthii* is named for the inventor, Hans Barth. In addition to growth habit, new Echinodorus differs from the species *Echinodorus barthii* in the following characteristics:

1. Plants of the new Echinodorus are more compact than plants of the species *Echinodorus barthii.*

2. Leaf color of plants of the new Echinodorus is lighter than leaf color of plants of the species *Echinodorus barthii.*

3. Leaves of plants of the new Echinodorus are narrower than leaves of plants of the species *Echinodorus barthii.*

4. Leaves of plants of the new Echinodorus are undulating and leaf apices are upturned whereas leaves of plants of the species *Echinodorus barthii* are flat.

The accompany colored photograph illustrates the overall appearance of the new cultivar, showing the colors as true as it is reasonably possible to obtain in colored reproductions of this type.

The first photograph comprises a top perspective view of a typical plant of 'Indian Red' in an aquatic environment.

The second photograph comprises a side perspective view of a typical plant of 'Indian Red' depicting foliage and root characteristics.

Foliage colors in the photograph may appear different from the actual colors due to light reflectance.

In the following description, color references are made To the Royal Horticultural Society Colour Chart except where general terms of ordinary dictionary significance are used.

Botanical classification: *Echinodorus aschersonianus*× *horemanii red* cultivar 'Indian Red'.

Parentage:

*Seed or female parent*.—An unnamed plant of *Echinodorus aschersonianus.*

*Pollen or male parent*.—An unnamed plant of *Echinodorus horemanii red.*

Propagation: By tissue culture and by adventitious shoots.

Plants grown in aerial or aquatic environments will develop numerous, thick, white, tapered roots.

Plant description:

*Plant shape*.—Upright, inverted triangle, symmetrical.

*Growth habit*.—Rosette with leaves erect. Runners, or adventitious shoots, and rhizomes may form.

*Plant height*.—Relatively compact, about 17 cm from plant base to top of leaf plane.

*Plant vigor*.—Moderate.

*Growth rate*.—Moderate.

*Crop time*.—About 8 weeks are required from an adventitious shoot to a 5-cm pot.

*Foliage description*.—Arrangement: Single leaves arranged in a rosette on long peticles. Quantity of leaves per finished plant: On average, about eight. Leaf shape: Elliptic to ovate. Leaf apex: Acute to rounded. Leaf base: Obtuse. Venation: Palmate, usually 3 or 5 primary veins with secondary veins arranged in a herringbone pattern from the central vein and extending to the margin crossing through the longitudinal veins. Veins on lower leaf surface prominent. Vein color consistently similar to yellowish-green ground color of the leaf. Margin: Entire. Leaf aspect: slight undulation. Undulation more pronounced on older leaves. Leaf texture: Glabrous. Glossy when wet, dull when dry. Leathery to membranous, translucent. Leaf size: Length: about 8.5 cm. Width: About 4.5 cm. Leaf color: Actual leaf color is a function of the environment. In an aerial environment, leaf coloration is in tones of green. When grown in an aquatic environment, leaf color is brownish red depending on leaf maturity. Increasing light intensity will also increase the brownish red coloration. Young foliage: upper and lower surfaces are transparent and yellowish-green, 146A. Mature, upper surface: Brownish red to dark green. Brownish red color closest to 180A/176A. Dark green color does not appear in The Royal Horticultural Society Colour Chart. Mature, lower surface: Brownish red, dulled, with dark green overtones. Petiole length: On average, about 8.5. Petiole color: Medium green, 144A to 146A with fine darker green annular stripes.

Flower description: Flowers are only formed on plants grown in an aerial environment. Plants form flowers under long photopeiods. Flowers formed are androgynous Inflorescences racemose, above the leaves, erect to slightly decumbent, with 5 to 8 whorls with numerous flowers and vegetative proliferations. Bracts acuminate, to about 1.5 cm long and about 7 mm wide. Flowers about 4 cm in width, slightly patellate, pedicels about 3.8 cm long. Sepals, three in number, green, about 8 mm by 4 mm. Petals, three in number, white, slightly overlapping, slightly emarginate, about 2.5 cm by 2.5 cm. Stamens, about 20 in number, anthers about 2 mm in length and filaments about 2.5 mm in length. Carpels numerous.

Disease resistance: No resistance to diseases has been noted.

Seed development: Seed development has not been observed.

It is claimed:

1. A new and distinct cultivar of Echinodorus plant named 'Indian Red', as illustrated and described.

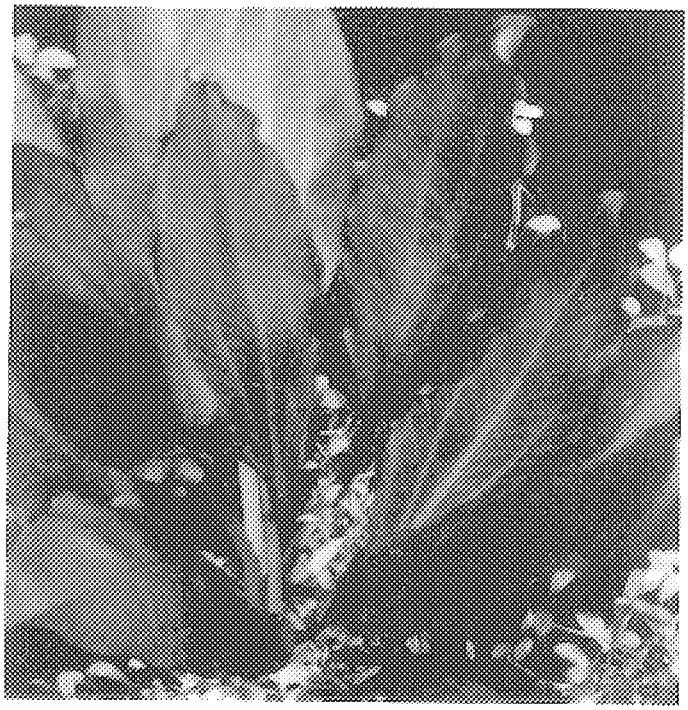

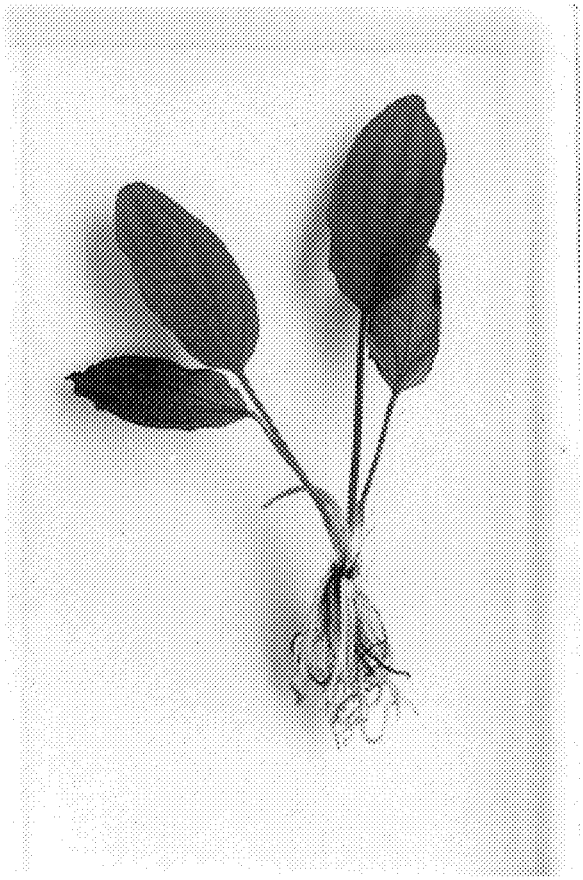

* * * * *